United States Patent [19]

Rolland

[11] Patent Number: 4,746,679

[45] Date of Patent: May 24, 1988

[54] NOVEL PHARMACEUTICAL COMPOSITIONS IMPROVING THE PSYCHOMOTOR PERFORMANCES AND A PROCESS FOR PRODUCING THE SAME

[76] Inventor: Anne Rolland, 45 rue Lamarck, 75018 Paris, France

[21] Appl. No.: 878,019

[22] Filed: Jun. 24, 1986

[30] Foreign Application Priority Data

Jun. 24, 1985 [FR] France ................. 85 09572

[51] Int. Cl.$^4$ ........................................... A61K 31/135
[52] U.S. Cl. ................................................. 514/646
[58] Field of Search ..................................... 514/646

[56] References Cited

PUBLICATIONS

Chem. Abst.—102-197462f, (1985).

Primary Examiner—Stanley J. Friedman
Attorney, Agent, or Firm—Omri M. Behr

[57] ABSTRACT

There is provided a method for alleviating the decrease of psychomotor performances in depressed or tired humans in need of such alleviation which consists in administering to such humans a safe but effective amount of 2,2-bis phenoxy-N,N-dimethyl ethylamine or an acid addition salt thereof.

2 Claims, No Drawings

ND A PROCESS FOR
NOVEL PHARMACEUTICAL COMPOSITIONS IMPROVING THE PSYCHOMOTOR PERFORMANCES AND A PROCESS FOR PRODUCING THE SAME

This invention relates to novel pharmaceutical compositions intended to amend or improve the psychomotor performances.

More particularly it has as subject matter novel pharmaceutical compositions intended to improve vigilancy or counter act the conditions connected to decrease of intellectual performances.

Specifically this invention provides pharmaceutical compositions having as active ingredient a neurologically-active amount of 2,2-bis phenoxy NN-dimethyl ethylamine (or Medifoxamine) or an acid addition salt thereof with a mineral or organic acid in admixture or conjunction with an inert, non-toxic, pharmaceutically-acceptable vehicle or carrier.

It has been surprisingly stated that in contrast to the usual actions of the anti-depressant agents or the anxiolytics agents, Medifoxamine does not cause a depression of the intellectual activity but further more is able to amend or improve the psychomotor performances in the depressed man.

It is already known that among the usual effects of the neurotrope substances such as tranquillizing agents, or of the psychotrope substances such as the anti-depressant drugs, one of the more noxious side-effects is the loss of attention or the decrease of the intellectual keenness. This is the reason why the physicians books mention at as a caution for use, the risk of sleepiness for the people which work at a machine or for the car drivers as well as the decrease in the ability of intellectual concentration.

As an example the French Medical Dictionary (VIDAL) mentions for most of the anti-depressant drugs or for the anxiolytic drugs the following statement as a caution: This drug may weaken the mental and physical capacities needed for the execution of some hard or dangerous work such as handling of machines or apparatus or driving of a motorized vehicle, risk of drowsiness.

It is therefore of value in the treatment of anxiety or of the depressive or maniaco-involutive psychosis—which need a protracted treatment to provide a medicine which alleviates this undesirable side-effects and allows the patient to keep a normal professional activity.

It is also worthwhile to be in a position to give to healthy subjects showing a risk of marked intellectual tiredness a medicine which allow them to keep at a normal level their psychomotor performances. This is for example the point for the workers which have to conduct machines for the night-watchmen, for the employees which remain at work for the night.

The compositions according to this invention, are given by parenteral way in the form of ampuls, multidoses flasks, auto-injectable syringes; by oral way as tablets, coated tablets, dragees capsules, soft gelatine capsules, pills, micro granules, drops drinkable solutions or suspensions; rectal way as rectal capsules or suppositories.

The carriers or vehicles which are the most suitables for such routes of administration are water or salines the starches, the microcrystalline celluloses, calcium, phosphate, magnesium, phosphate, magnesium stearate, Talc, Carboxymethyl celluloses, poly Vinyl pyrrolidones, Cacao butter or poly(ethyleneglycol)stearates.

The usual dosology ranges from 40 to 200 mg Medifoxamine per u dosage and preferably from 40 to 60 mg of Medifoxamine. The daily doses range from 200 to 400 mg of active-ingredient divided in one to four takings.

The dosology may broadly vary depending on the weight of the patient, the age of the patient, on the therapeutic use and the route of administration.

This invention also extends to a process for producing the pharmaceutical compositions for improving the psychomotor performances as, which consists in that an active amount of Medifoxamine or an addition salt thereof is added or admixed to one or several inert, non-toxic pharmaceutically-acceptable carrier or vehicle.

The following examples illustrate this invention without limiting it in any manner.

EXAMPLE I

| Tablets containing 50 mg Medifoxamine as the fumarate | |
|---|---|
| Medifoxamine Fumarate | 70.4 g |
| Wheat starch | 45 g |
| Maize starch | 60 g |
| Microcrystalline Cellulose | 5 g |
| Methylene caseine | 4.6 g |
| Magnesium stearate | 12 g |
| Talc | 3 g |
| for 1000 Tablets having a mean weight of 2 g | |

EXAMPLE II

Studies on psychomotor performances of Medifoxamine (tablets at 50 mg).

This study has been carried out with the purpose to evaluate the effects of Medifoxamine at 50 mg given at repeated dosages for 4 days, on tasks requiring attention or vigilancy and on tests of immediate remembrance in the evaluation of the psychomotor performances of a human operator.

METHOD

Evaluation of the psychomotor performance

The performance in the man has been determined on one part using a complexe psychomotor task connecting a main task of visual pursuance drawn along two axes called "tracking" and a secondary task of measuring times for reacting to a visual stimulis and an the other part, using a test requiring immediate remembrance described by DE FAYOLLE and called VIGIL 97.

"Tracking"

The visual informations on which the main task of tracking is based are presented on a screen adapted from an aeronautic device for assistance in case of landing by poor visibility (ILS)—This screen with two crossed hands is located on metallic frame-work, in front to the operator and at about 0.7 m from his eyes.

The hands corresponding each to a horizontal or vertical axis move according to a pre recorded programm on a magnetic tape.

It appears to be two sinusoids of constant peak power and variable frequency comprised between 0.1 and 0.05 $H_z$ and out of phase each other.

During the performance of the test, the duration of which has been fixed at 10 mm, the volunteer must maintain the two orthogonal hands at the middle of the screen by means of a very small joy-stick located before him on a table.

The variations in the positions of the two hands with regard to the vertical and horizontal axes form the mistakes made by the subject.

The data are treated in an analogic calculating machine which provides after summation of the variations, a score of mistakes expressed in Unities-Machine for the set of 10 mm, comparing the performance of the subject and the optimal performance previously memorized.

This calculation of the mistakes is distinctly operated for the sight (vertical axis or localizer) and for the bearing (horizontal axis or glide)

Total Time of Reaction

During the test of tracking the subject has to perform a minor task of detecting and switching off light signals. They are two lamps located on a horizontal axis at the level of the eyes of the subject and in the same plane than the ILS Dial, at 0.45 m on both directions from the ltter. The left lamp is red. The right lamp is green. They catch alight distinctly one from the other and in aleatory manner.

As soon as a signal is perceived, the subject has to press an operating button located on a grip maintained in the hand which is not engaged in the Tracking test.

During the test period of 10 mm which is simultaneous with the tracking task, 16 signals are provided. The time intervalls between two successive lightnings vary in an aleatory manner from 25 to 60 secondes. The periods from the lightning to the switching off the lamps are measured with accuracy of about ±5 ms.

This time is visualized on a digital voltmeter and automatically recorded on paper in a numeric form. For each test a mean switching-off time of the coloured lights is calculated.

Test of Memorization

The VIGIL 97 Test is a test of memorization which allows to evaluate the mean span of the immediate memory. It is prerecorded and offered in a desk microcalculating machine—Hewlett Packard HP 97). Whatever number is presented twice consecutively to the subject for one second; the two displays succeed in a quasi-instantaneous manner.

As soon as the numerical value appears on the screen, the subject has to reproduce the displayed figures by means of the finger-board of the calculating machine—If this response is right, whatever number incremented of a value anew is offered to the subject in the same conditions and so forth.

At the contrary, when the response is wrong, what ever number decremented of a value, is anew offered. A sequence includes the display of ten different numbers.

The tested subject has to respond to two consecutive sequences.

For each sequence the programm allows the calculation of the mean span of the memory expressed in numbers of memorized figures and the variability thereof.

METHOD

The study has been performed in 12 adults volunteers of male sex, 22 to 49 years old and the weight of which ranged from 65 to 78 Kg. The subjects volunteers and healthy, are used to spend an active life, are well-trained and familiar with the above-described psychomotor tasks for a long time.

During the period of testing performed under strict monotherapy, the subjects avoid taking any psychostimulant or exciting drug the day of experiment; the ingestion of any spirit is forbidden during the sequences of testing.

The study has been carried out in doubleblind. Each subject included in this study has been his own control and received a number corresponding to the randomization of the two established sequences of treatment, one corresponding to MEDIFOXAMINE at 50 mg, the other to a placebo given in the same package.

Each subject was given for three days:
2 tablets containing MEDIFOXAMINE at 50 mg or a placebo before the meal in the morning.
2 tablets containing 50 mg MEDIFOXAMINE or a placebo before the mid-day lunch.
2 tablets containing 50 mg MEDIFOXAMINE or a placebo before the meal at the evening then on the fourth day:
2 tablets containing 50 mg MEDIFOXAMINE or a placebo before the meal in the morning.

The psychomotor tests have been performed between 1 and 3 hours after the sole taking of a drug on the 4th day of treatment.

Each subject alternatively has effected two series of each test: before taking any compound then between 1 and 3 hours after the last administration of tablets of 50 mg MEDIFOXAMINE or of a placebo.

The tests conducted in the subjects at days $D_1$ and $D_{15}$ before the administration and at days $D_4$ and $D_{18}$ after the administrations were identical and successively consisted in two taskes of separated tracking followed with a DE FAYOLLE'S Test.

Statistical Methodology

The statistical treatment of the obtained results invoked the theory of analysis of variance.

Under the double hypothesis of normality of distributions and independance between averages and variances, the calculation of analysis of variance has been carried along a plan is crossed factors.

Three qualitative factors have beed used-one of this corresponds to the organization of the experimental protocol in full blocks, one of these blocks relates to a subject. It appears then to be the effect "subject".

The second of this reports to the influence of the given drug in four different situations:
1st test of reference
2nd test of reference
Placebo
Tablets of Medifoxamine at 50 mg (called compound C).

This last factor finally makes into account the timely evolution of the psychomotor performance throughout the test since two sets of tests have been successively offered during each experiment.

In other words this factor reports to the effect "tiredness".

The analysis also allows the evaluation of the signification of the parameter interaction of the two experimental factors "drug" and "tiredness". This test thus allows to evaluate the reciprocal influence of these two factors each on the other. Otherwise it allows to answer the question to know whether the tiredness, occured during the performance of the experiment, is constant as regard the given "drug" or not.

The other statistical tests are included within the aleatory error. The results of these various evaluations are given according to the F-Test of Fischer-Snedecor.

After evaluation of the signification of each of the taken experimental factors, a more precise analysis of the results is carried out in the form of a comparison of the various means two by two.

The chosen test is the T. test of Student or the G. Test said Test of "studentized Range" according to the conditions of application, respective for these two tests.

The denominator for each of these two tests utilizes the aleatory error as determined by the analysis of variance.

RESULTS

Test of Tracking

The numerical dater of the test of Tracking are the sum of the scores realized on each of the horizontal and vertical axes.

The calculations show
an effect "subject" very markedly significative- $F(11.77)=322$
an effect "drug" significative at a risk of 1 p.cent $F(3.77)=5.07$ The respective means correlated to a standard deviation of 6.9, are equal to:

| | |
|---|---|
| reference test 1 | 309.5 |
| reference test 2 | 309.5 |
| placebo | 308.6 |
| compound C (ie. MEDIFOXAMINE) | 293.4 |

They are significative differences two to two between:
reference test 1 and MEDIFOXAMINE t=3.25
reference test 1 and MEDIFOXAMINE t=3.23
placebo and MEDIFOXAMINE t=3.06

In contrast thereof, the two reference values and the averages of the scores with placebo are very close each other.

The effect "tiredness" is not significative $F(1.77)=0.36$ and the test of interaction "Drug-Time" is not also significative $F(3.77)=0.07$

DE FAYOLLE'S TEST

The numerical data of this test have been submitted to the same evaluation according to the same process as previously; with the only restriction that the factor "Tiredness" includes four levels corresponding to the four experiments performed during the test (two sequences and two testings).

The effect "subject" is markedly significative $F(11.165)=10.93$

The effect "drug" is significative at the risk of 2 percent $F(3.165)=3.48$

The mean values, correlated to a standard deviation of 0.1 are respectively equal to:

| | |
|---|---|
| reference test 1 | 6.9 |
| reference test 2 | 7.1 |
| placebo | 7.0 |
| MEDIFOXAMINE | 7.1 |

It is no at 50 mg statitiscally significative difference between Placebo and MEDIFOXAMINE at 50 mg.

The effect "tiredness" is not significative:

$F(3.165)=0.34$

The test of interaction "drug-triedness" is not statistically-significative:

$F(9.165)=0.54$

CONCLUSION

The studies performed at 12 adults male subjects have evidemed the fact that MEDIFOXAMINE tablets at 50 mg administered for 3 days at the daily dosage of 3 times two tablets do not induce any noxious side-effect on the level of vigilancy in a human worker.

In the contrary the test of compensated tracking, taken in this method as the main psychomotor task, is statistically-significantly improved by the tablets of MEDIFOXAMINE at 50 mg.

What is claimed is:

1. A method for alleviating the decrease of psychomotor performance in depressed or tired humans in need of such alleviation which consists in administering to such humans a safe but effective amount of 2,2-bis phenoxy-NN-dimethyl ethylamine or an acid addition salt thereof.

2. The method of claim 1 wherein the amount of 2,2-bis phenoxy N,N-dimethyl ethylamine or of an acid addition salt thereof ranges from 200 to 400 mg per day in the adult human.

* * * * *